(12) United States Patent
Lee et al.

(10) Patent No.: US 11,029,271 B2
(45) Date of Patent: Jun. 8, 2021

(54) AMMONIA GAS DETECTING SENSOR USING GRAPHENE DOPED WITH COPPER OXIDE NANOPATICLES AND AMMONIA GAS DETECTING DEVICE COMPRISING THE SAME

(71) Applicant: KOREA INSTITUTE OF SCIENCE AND TECHNOLOGY, Seoul (KR)

(72) Inventors: Kang Bong Lee, Seoul (KR); Yun Sik Nam, Seoul (KR); Yeon Hee Lee, Seoul (KR); Oleksandr Tsymbalenko, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 234 days.

(21) Appl. No.: 16/255,433

(22) Filed: Jan. 23, 2019

(65) Prior Publication Data
US 2020/0124555 A1    Apr. 23, 2020

(30) Foreign Application Priority Data
Oct. 19, 2018   (KR) .................. 10-2018-0125015

(51) Int. Cl.
*G01N 27/12* (2006.01)
*G01N 33/00* (2006.01)

(52) U.S. Cl.
CPC ....... *G01N 27/127* (2013.01); *G01N 33/0054* (2013.01)

(58) Field of Classification Search
CPC ............. G01N 27/127; G01N 33/0054; G01N 27/4071; G01N 27/4074; Y02A 50/20; B82Y 30/00; C01B 32/186; C01B 32/194; C01G 3/02; C01P 2004/64
See application file for complete search history.

(56) References Cited

U.S. PATENT DOCUMENTS

| | | |
|---|---|---|
| 9,133,549 B2 * | 9/2015 | Kim .................. C23C 24/04 |
| 9,874,541 B2 * | 1/2018 | Raguse ............ G01N 27/4146 |
| 10,024,831 B2 * | 7/2018 | Ruhl ................ G01N 33/004 |
| 2014/0377790 A1 * | 12/2014 | Ramaprabhu .... G01N 33/54346 435/20 |

(Continued)

FOREIGN PATENT DOCUMENTS

| | | | |
|---|---|---|---|
| DE | 102016110786 A1 * | 12/2017 | .......... G01N 27/121 |
| KR | 10-2014-0015897 A | 2/2014 | |
| KR | 10-2017-0131155 A | 11/2017 | |

(Continued)

OTHER PUBLICATIONS

Lee, K.-B. "Chemiresistive ammonia gas sensor based on graphene decorated with CuO nanoparticles," Graphene2018, Dresden, Germany (2018) (1 page).

(Continued)

*Primary Examiner* — Matthew D Krcha
*Assistant Examiner* — Sophia Y Lyle
(74) *Attorney, Agent, or Firm* — Birch, Stewart, Kolasch & Birch, LLP

(57) ABSTRACT

The present disclosure relates to an ammonia gas detection sensor including a substrate, a graphene sheet disposed on the substrate, and metal nanoparticles disposed on the graphene sheet, and an ammonia gas detection device comprising the gas detection sensor.

6 Claims, 26 Drawing Sheets

(56) References Cited

U.S. PATENT DOCUMENTS

2018/0136157 A1* 5/2018 Harada .............. G01N 27/4146

FOREIGN PATENT DOCUMENTS

| KR | 10-1851281 B1 | 6/2018 | | |
|---|---|---|---|---|
| KR | 10-1898584 B1 | 9/2018 | | |
| WO | WO-2014180919 A1 * | 11/2014 | ............... | C09K 5/14 |
| WO | WO-2017002854 A1 * | 1/2017 | ......... | G01N 33/0054 |

OTHER PUBLICATIONS

Zhang et al., "Hydrogen gas sensor based on metal oxide nanoparticles decorated graphene transistor," Nanoscale (2015), vol. 7, pp. 10078-10084.

Yin et al., "A hydrogen peroxide electrochemical sensor based on silver nanoparticles decorated silicon nanowire arrays", Electrochimica Acta, vol. 56, 2011, pp. 3884-3889.

Zhao et al., "A novel nonenzymatic hydrogen peroxide sensor based on multi-wall carbon nanotube/silver nanoparticle nanohybrids modified gold electrode", Talanta, vol. 80, 2009, pp. 1029-1033.

* cited by examiner

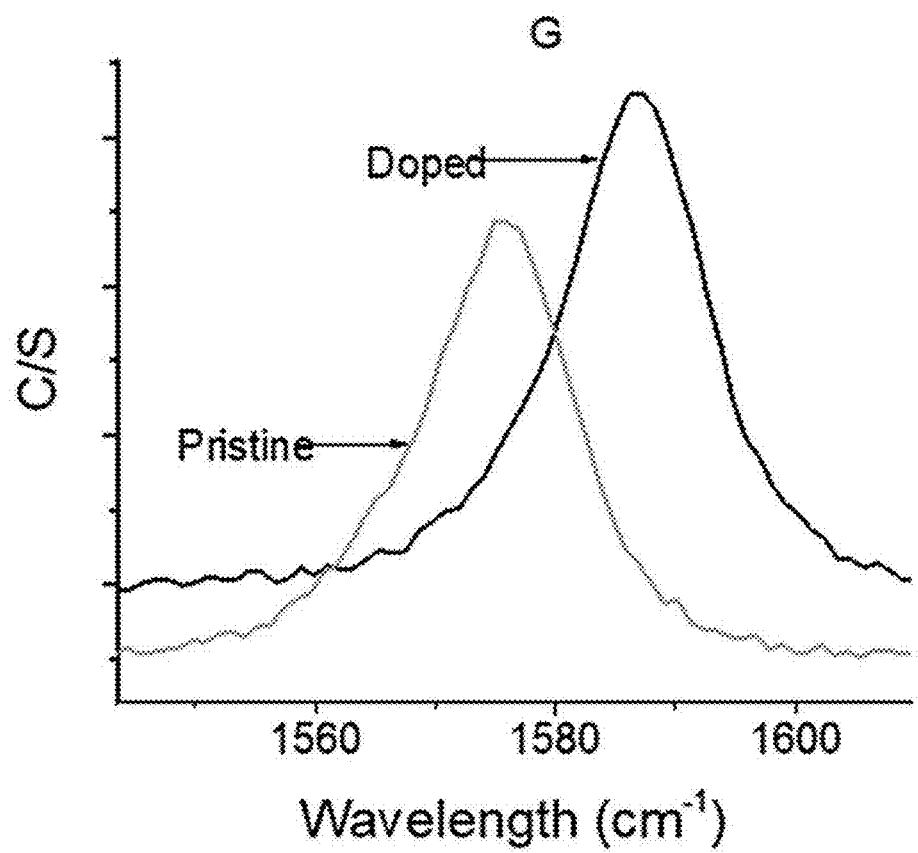

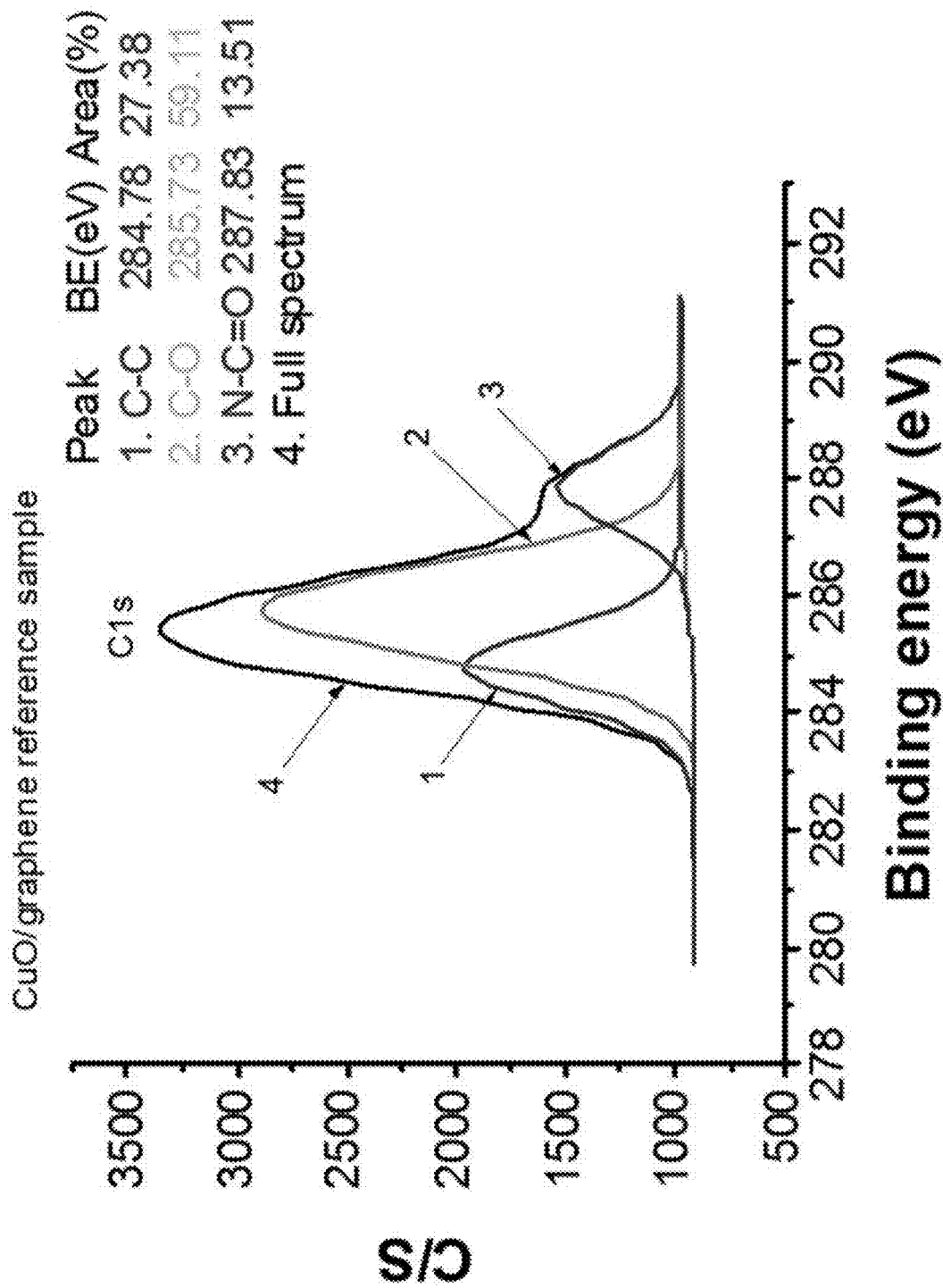

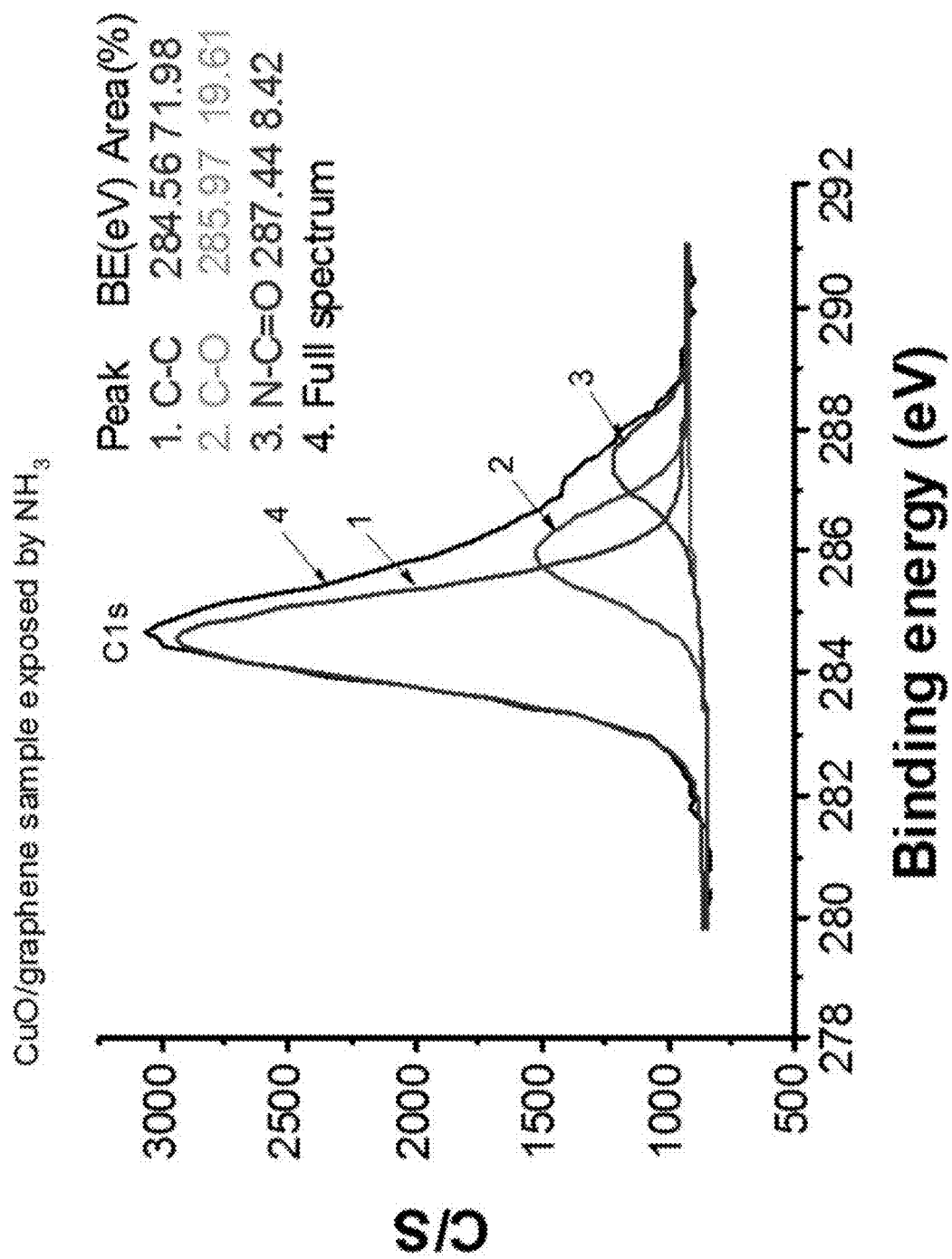

AMMONIA GAS DETECTING SENSOR USING GRAPHENE DOPED WITH COPPER OXIDE NANOPATICLES AND AMMONIA GAS DETECTING DEVICE COMPRISING THE SAME

CROSS-REFERENCE TO RELATED APPLICATION

This application claims priority to Korean Patent Application No. 10-2018-0125015, filed on Oct. 19, 2018, and all the benefits accruing therefrom under 35 U.S.C. § 119, the contents of which in its entirety are herein incorporated by reference.

BACKGROUND

1. Field

The present disclosure relates to an ammonia gas detection sensor and an ammonia gas detection device, and more particularly, to an ammonia gas detection sensor and an ammonia gas detection device for detecting ammonia with high sensitivity and high selectivity using the fact that graphene doped with copper oxide (CuO) nanoparticles changes in the properties of graphene electrically and chemically when in contact with ammonia gas.

[Explanation of National-Supported Research and Development]

This study was supported by the Public Technology Development Project based on the environmental policy of Ministry of Environment, Republic of Korea (Real-time field detection technology for bioaerosol and harmful heavy metal components in ultrafine dust and fine dust, Project No. 1485015514) under the Korea Environmental Industry and Technology Institute.

2. Description of the Related Art

Ammonia gas ($NH_3$) is mainly produced in the fields of animal husbandry, agriculture, waste treatment plants, sewage treatment plants, complex compost production and starch production, and in the process of production of organic and inorganic pharmaceuticals.

Because ammonia gas is toxic and harmful to human body in the event of leaks in large amounts, ammonia gas sensors need to measure the ammonia gas concentration at the site, not only in the above-described sources of emissions but also in many ammonia gas emission fields including chemical engineering, food technology, thermoelectric power plants, environmental protection, medical diagnosis and industrial processes.

Metal oxide based chemical sensors have high power consumption due to high temperature operating characteristics, and to solve this problem, they use carbon nanotubes, graphene oxide or reduced graphene oxide, but very low sensitivity is their drawback.

Additionally, many types of gas sensors based on metal oxide, conductive polymer, field effect transistor and acoustic wave are widely known, but among these sensors, the most attention is paid to sensors using semiconductors.

In particular, graphene has been studied for various applications since its discovery in 2004, and research has been made on the use of high efficiency sensors and adsorbents to meet the demand for clean environment in real life applications and easily detect and remove toxic gas including ammonia gas in the industry.

Additionally, vacancy defects in graphene and defects caused by substitution occur during production of graphene. By exploiting this physical property of graphene devices, it is possible to use as gas sensor devices.

Additionally, due to high electrical conductivity and the presence of multiple surface atoms, the movement of electrons to absorbed and desorbed gas molecules is very sensitive, and this is the reason that monolayer graphene attains much attention, and accordingly, graphene has unique electrical properties and high surface area, and when doped with metal oxide, it changes in the properties and thus can be used in many fields.

RELATED LITERATURES

Patent Literatures

Patent Literature 1: Korean Patent Application Publication No. 10-2017-0131155

Patent Literature 2: Korean Patent Publication No. 10-1851281

SUMMARY

For example, a gas detection sensor 1000 of Patent Literature 1 shown in FIG. 16 is a sensor for gas measurement, manufactured by binding fluorine atoms to graphene oxide.

However, the gas detection sensor 1000 of Patent Literature 1 can measure not only ammonia gas but also nitrogen ($N_2$) gas and hydrogen gas, and due to this, it lacks selectivity of gas measurement, and most of all, after measurements, the sensor recovery time is 2000 sec or longer, which makes it difficult to measure ammonia gas at the site in real time.

Additionally, a gas detection sensor 2000 of Patent Literature 2 shown in FIG. 17 measures gas using conductivity of oxygen ions.

However, the gas detection sensor 2000 of Patent Literature 2 also has a limitation in improving the responsivity to ammonia concentrations.

Accordingly, there is a need for development of an ammonia gas detection sensor for improving the reactivity, responsivity and recovery of a measurement sensor through graphene modification.

To achieve the above-described object, the present disclosure may provide an ammonia gas detection sensor including a substrate, a graphene sheet disposed on the substrate, and metal nanoparticles disposed on the graphene sheet.

Additionally, the ammonia gas detection sensor of the present disclosure may detect a gaseous ammonia gas, and the metal nanoparticles of the present disclosure may include copper oxide (I) (CuO) nanoparticles.

Additionally, the graphene sheet of the present disclosure may be a monolayer, and may be formed by deposition on the substrate by a chemical vapor deposition method.

Additionally, the copper oxide nanoparticles of the present disclosure may have a size of 10 nm to 20 nm.

Additionally, the copper oxide nanoparticles of the present disclosure may be formed by doping a mixed solution including copper oxide (I) (CuO) nanoparticles onto the graphene sheet, and the doping may include dipping the graphene sheet in the mixed solution and stirring the mixed solution by rotation at 1000 rpm to 2000 rpm.

Additionally, the mixed solution of the present disclosure may include 1 wt % to 2 wt % of copper oxide nanoparticles based on the total weight.

Additionally, the present disclosure may provide an ammonia gas detection device including the above-described ammonia gas detection sensor, electrodes connected to two ends of the graphene sheet, and a power supply unit which operates the ammonia gas detection sensor.

The present disclosure provides an ammonia gas detection sensor with high sensitivity and high selectivity that can be easily used even at room temperature, and is easy to manufacture, and an ammonia gas detection device comprising the sensor.

Additionally, the present disclosure provides an ammonia gas detection sensor and an ammonia gas detection device with high sensitivity, high selectivity, fast saturation and short recovery time.

BRIEF DESCRIPTION OF THE DRAWINGS

FIG. 5A to FIG. 5C are Raman spectrums of a graphene sheet doped with copper oxide nanoparticles according to an embodiment of the present disclosure.

FIG. 10A to FIG. 10E are XPS graphs showing, in an ammonia gas detection sensor according to an embodiment of the present disclosure, the observations of the binding reaction structure of pristine graphene and graphene doped with particles of copper oxide with ammonia gas responsive sensors.

DETAILED DESCRIPTION

Hereinafter, an ammonia gas detection sensor 10 according to an embodiment of the present disclosure and an ammonia gas detection device comprising the same will be described through the preferred embodiments of the present disclosure on the basis of the accompanying drawings.

Prior to the description, in many embodiments, the elements having the same configurations will be representatively described in an embodiment using the same reference signs, and in other embodiments, only different elements will be described.

Figure 1:
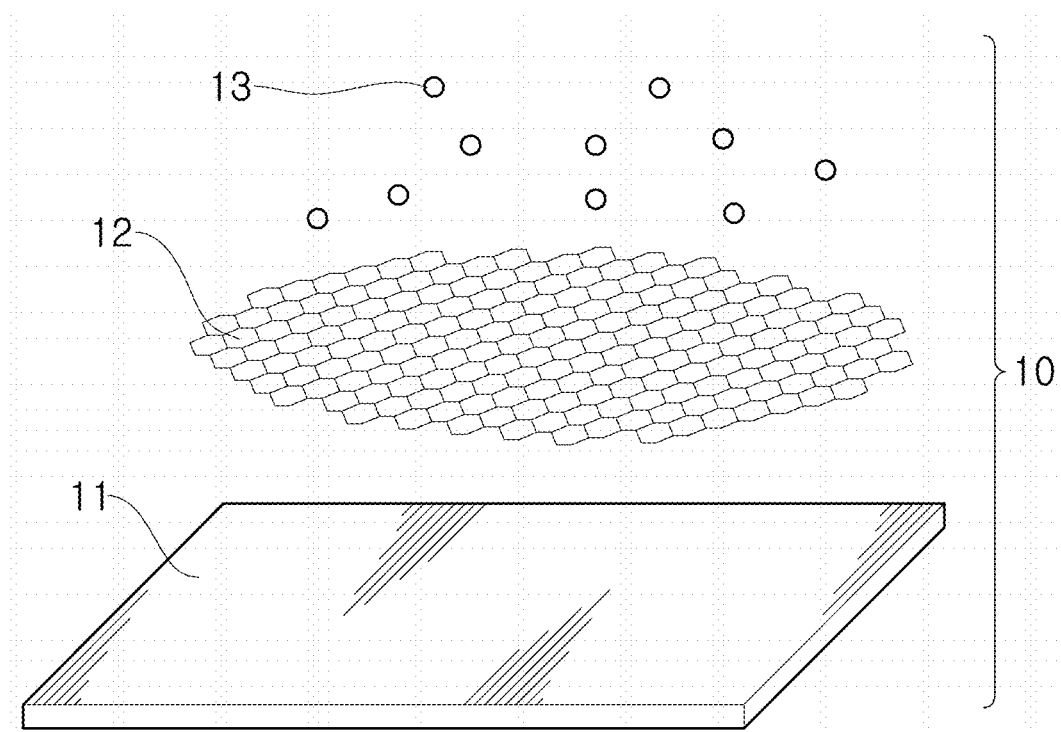
FIG. 1 is a schematic conceptual diagram showing a configuration of an ammonia gas detection sensor according to an embodiment of the present disclosure.

FIG. 1 is a schematic conceptual diagram showing the configuration of the ammonia gas detection sensor 10 according to an embodiment of the present disclosure.

As shown in FIG. 1, the ammonia gas detection sensor 10 according to an embodiment of the present disclosure includes a substrate 11, a graphene sheet 12 disposed on the substrate 11, and metal nanoparticles 13 disposed on the graphene sheet 12, and the metal nanoparticles 13 include copper oxide (CuO) nanoparticles. In particular, the ammonia gas detection sensor 10 according to an embodiment of the present disclosure is useful in detecting gaseous ammonia gas.

Figure 2:
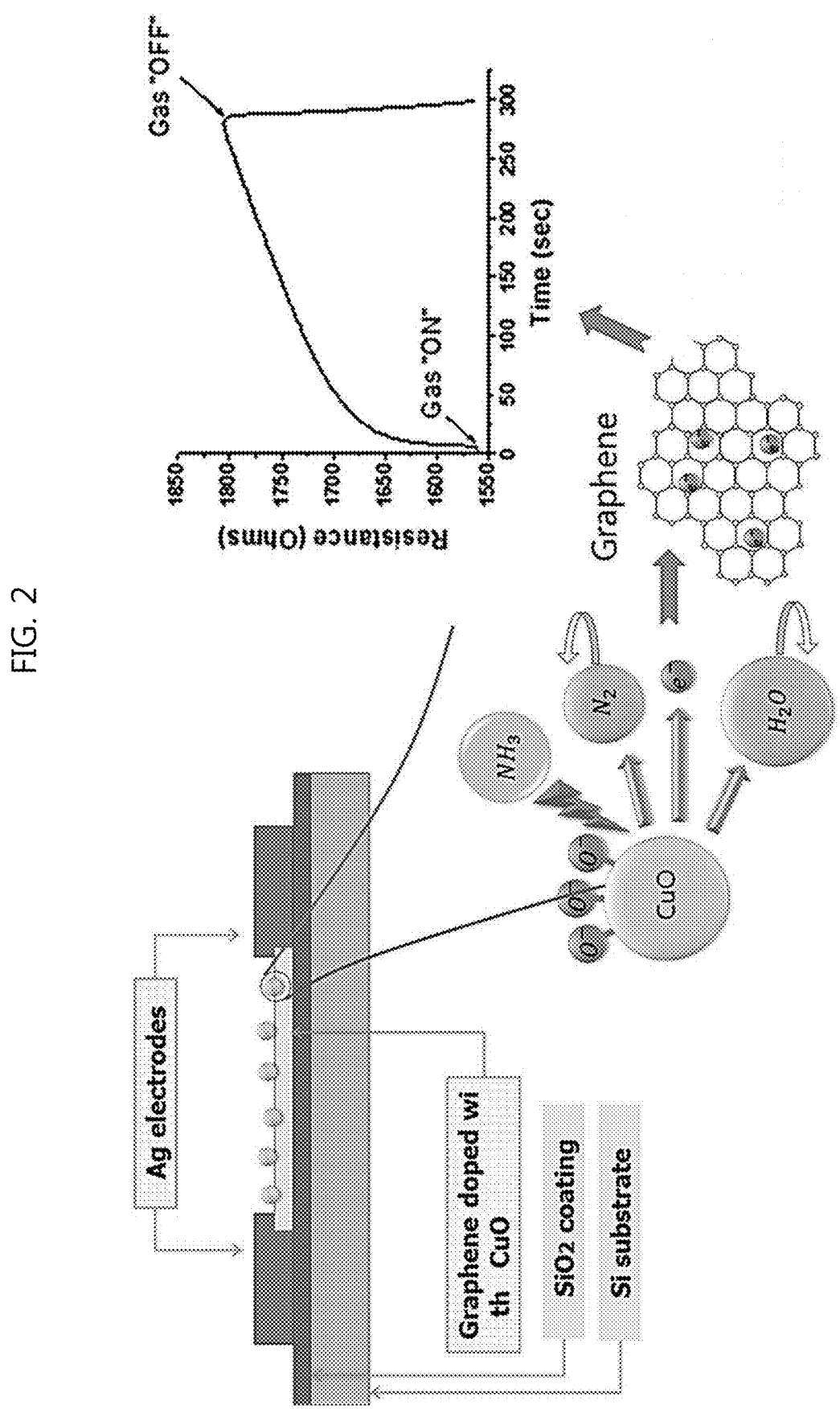
FIG. 2 is a schematic conceptual diagram showing a response process of an ammonia gas detection sensor according to an embodiment of the present disclosure.

FIG. 2 is a schematic conceptual diagram showing a response process of the ammonia gas detection sensor 10 according to an embodiment of the present disclosure.

In general, graphene in air has the p-type conducting property when oxygen and water vapor are adsorbed onto the surface, inducing electron expansion. The sensing mechanism on CuO surface may be described according to the following steps:

$$O_2(gas) \rightarrow O_2(ads) \quad (1)$$

$$O_2(ads) + e^- \rightarrow O_2^-(ads) \quad (2)$$

$$O_2(ads) + 2e^- \rightarrow 2O^-(ads) \quad (3)$$

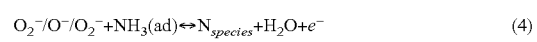

$$O_2^-/O^-/O_2^- + NH_3(ad) \leftrightarrow N_{species} + H_2O + e^- \quad (4)$$

The detailed interaction in Formula (4) may be described as different charge exchanges as below:

$$3O_2 + 4NH_3 \rightarrow 2N_2 + 6H_2O + 3e^- \quad (4.1)$$

$$3O^- + 2NH_3 \rightarrow N_2 + 3H_2O + 3e^- \quad (4.2)$$

$$3O_2^- + 2NH_3 \rightarrow N_2 + 3H_2O + 6e^- \quad (4.3)$$

Reaction (1) to (3) show the interaction of the sensor in ambient air in which oxygen is adsorbed onto the surface, inducing electron trapping. Additionally, reactions (4.1) to (4.3) are major sensing reaction. The adsorbed ammonia molecules and surface oxygen species eventually react with $N_2$ and $H_2O$ molecules as shown in FIG. 2.

The emitted electrons reduce the hole concentration of copper oxide nanoparticles. As CuO p-type semiconductor recombination of electrons and holes increases, the resistance increases. Additionally, in the case of a CuO-doped graphene sensor, the releasing process in ambient air requires about a few seconds.

Figure 3:
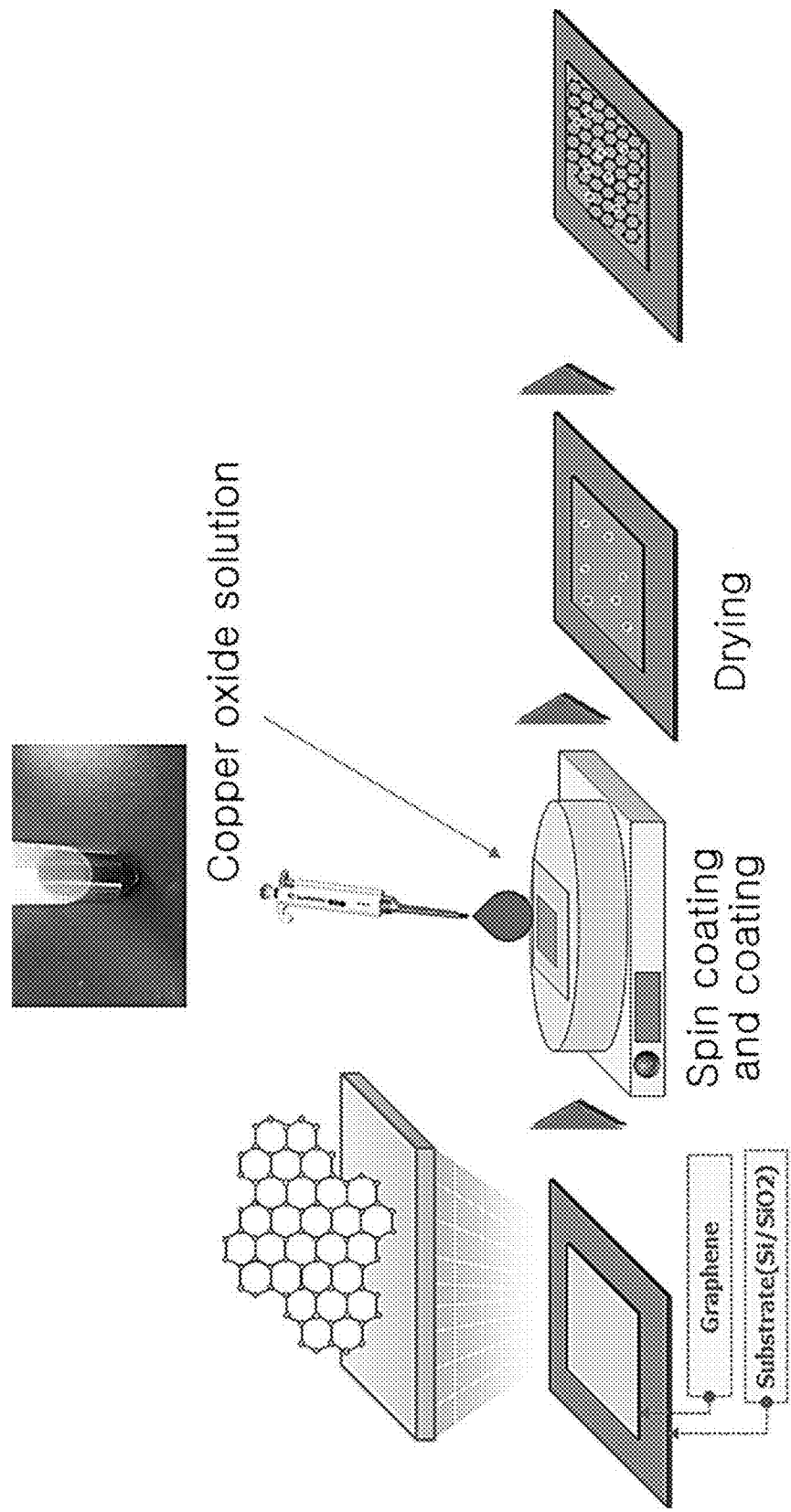
FIG. 3 is a schematic conceptual diagram showing a method for manufacturing an ammonia gas detection sensor according to an embodiment of the present disclosure.

FIG. 3 is a schematic conceptual diagram showing a method for manufacturing the ammonia gas detection sensor 1 according to an embodiment of the present disclosure.

As shown in FIG. 3, doping of graphene with CuO nanoparticles may be performed by adding 20 μL of 1 wt % to 2 wt %, preferably 0.12 wt % to 1.2 wt % CuO aqueous solution, and spin coating of $Si/SiO_2$ graphene.

In this instance, CuO nanoparticles were produced in various sizes of 10 nm to 80 nm, and preferably 10 nm to 20 nm, and in the case of spin coating, the rotational speed of the spin coater was variously adjusted to 0 to 4500 rpm.

After spin coating of graphene, the graphene sample was dried in an oven of 100° C. for 30 minutes to remove water from the surface. After heating, the produced CuO-graphene composite was cooled for 1 hour, and mounted in a plastic frame and connected to silver electrodes. The entire sensor manufacturing process is the same as FIG. 3.

To see surface characterization and structure of the CuO nanoparticles-doped graphene sensor, Raman, TEM, SEM, EDX, XPS equipment was used.

A surface composition analysis was performed using XPS (PHI 5000 VersaProbe, Ulvac-PHI, Japan), and a graphene quality test used Raman spectroscope (Renishaw, Gloucestershire, UK), in the range of 1300 to 3000 $cm^{-1}$. High solution images of pure and doped graphene could be obtained using transmission electron microscope (TEM) (FEI Talos, Oreg., USA) combined with Energy Dispersive Spectrometer (EDS).

To test the characteristics, sensitivity and performance of the ammonia sensor, the present disclosure mixed $NH_3$ and other gas with Ar using a gas diluter, and additionally diluted using argon gas (Ar purity: 99.999%).

The flow rate of the diluted Ar was adjusted by a gas mixing system, and the total gas flow rate was maintained at 5 $Lmin^{-1}$. In an embodiment of the present disclosure, initially, the baseline resistance was measured by exposure to ambient air, followed by exposure to ambient air again for recovery.

The CuO nanoparticles-doped graphene sensor may be of chemical resistant type. In this case, graphene is a semiconducting base and serves as a transducer. The reason why graphene was selected is that graphene has excellent resistance in the capability of working in severe environment, high conductivity, low temperature noise and ambient environment.

CuO nanoparticles were doped onto the graphene surface. To manufacture a chemical resistant sensor, it is necessary to make a contact using silver. Subsequently, the sensor was connected to a resistance measurement system (VersaSTAT 3, Ametec Inc., Berwyn, Pa., USA).

In the case of measurements, first, the resistance of the sensor in air was measured, and the sensitivity of the sensor may be described as below:

$$R\ (\%) = (R_r - R_i)/R_i \times 100\%$$

Here, $R_r$ is the resistance of the sensor measured in the presence of $NH_3$, and $R_i$ is the initial resistance of the sensor measured when there is no target gas to be analyzed.

FIG. 4A to FIG. 4D are diagrams showing a property of copper oxide nanoparticles according to an embodiment of the present disclosure.

Figure 4A:
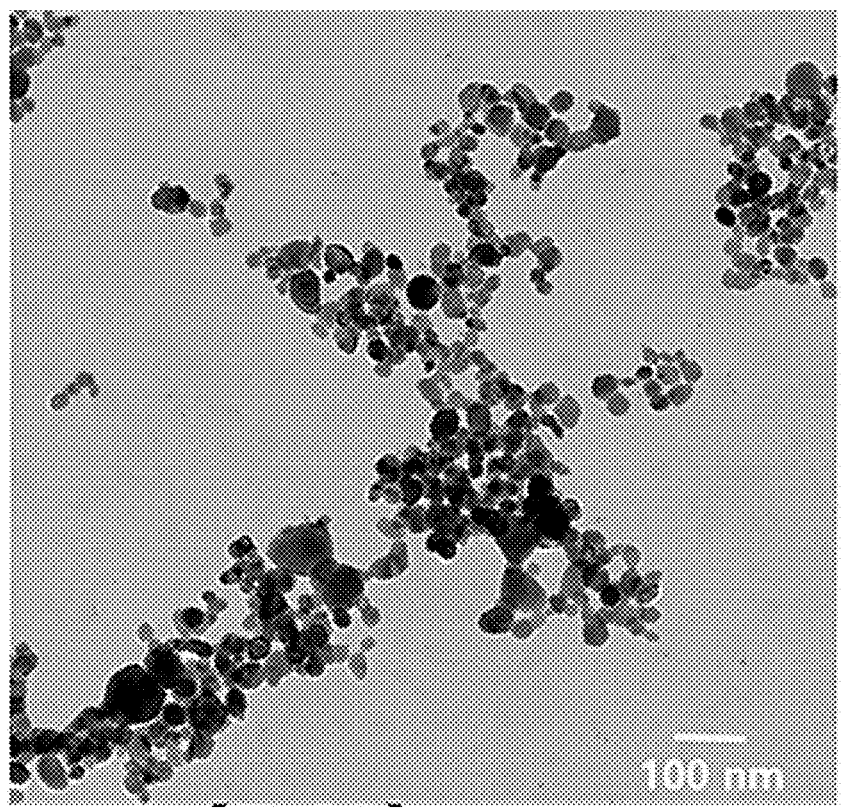
FIG. 4A to FIG. 4D show properties of copper oxide nanoparticles according to an embodiment of the present disclosure.
Figure 4B:
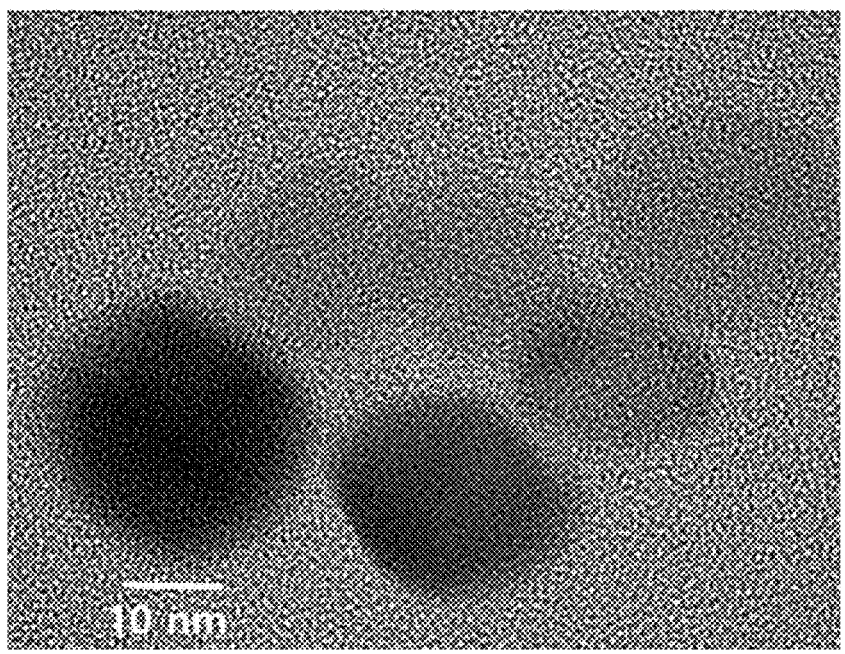
Figure 4C:
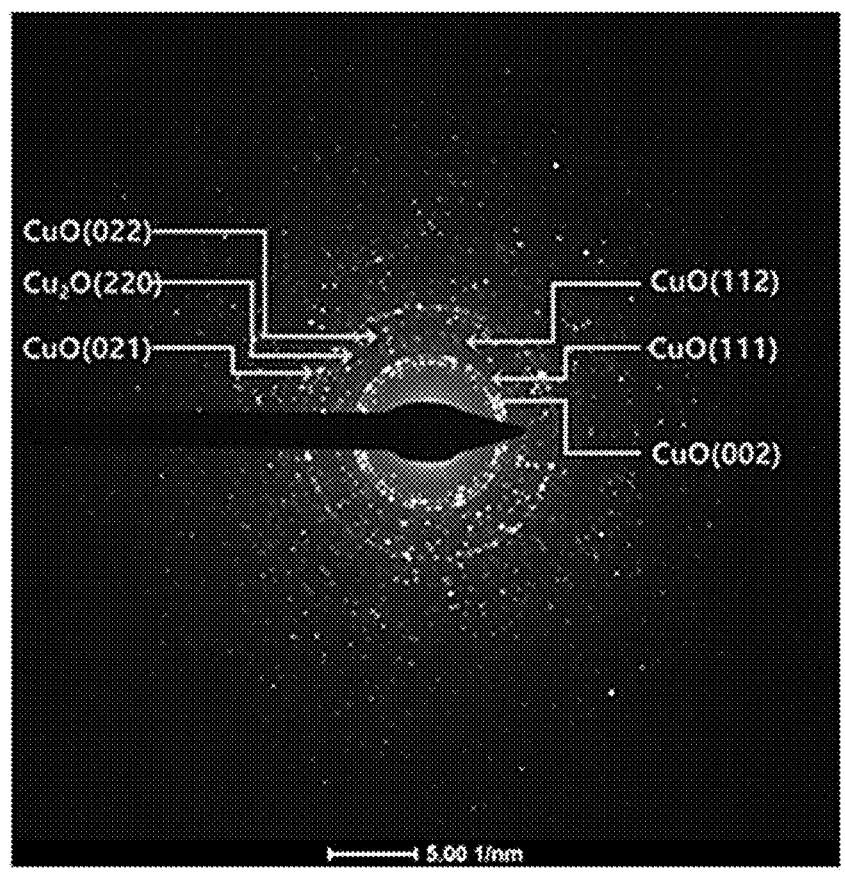
Figure 4D:
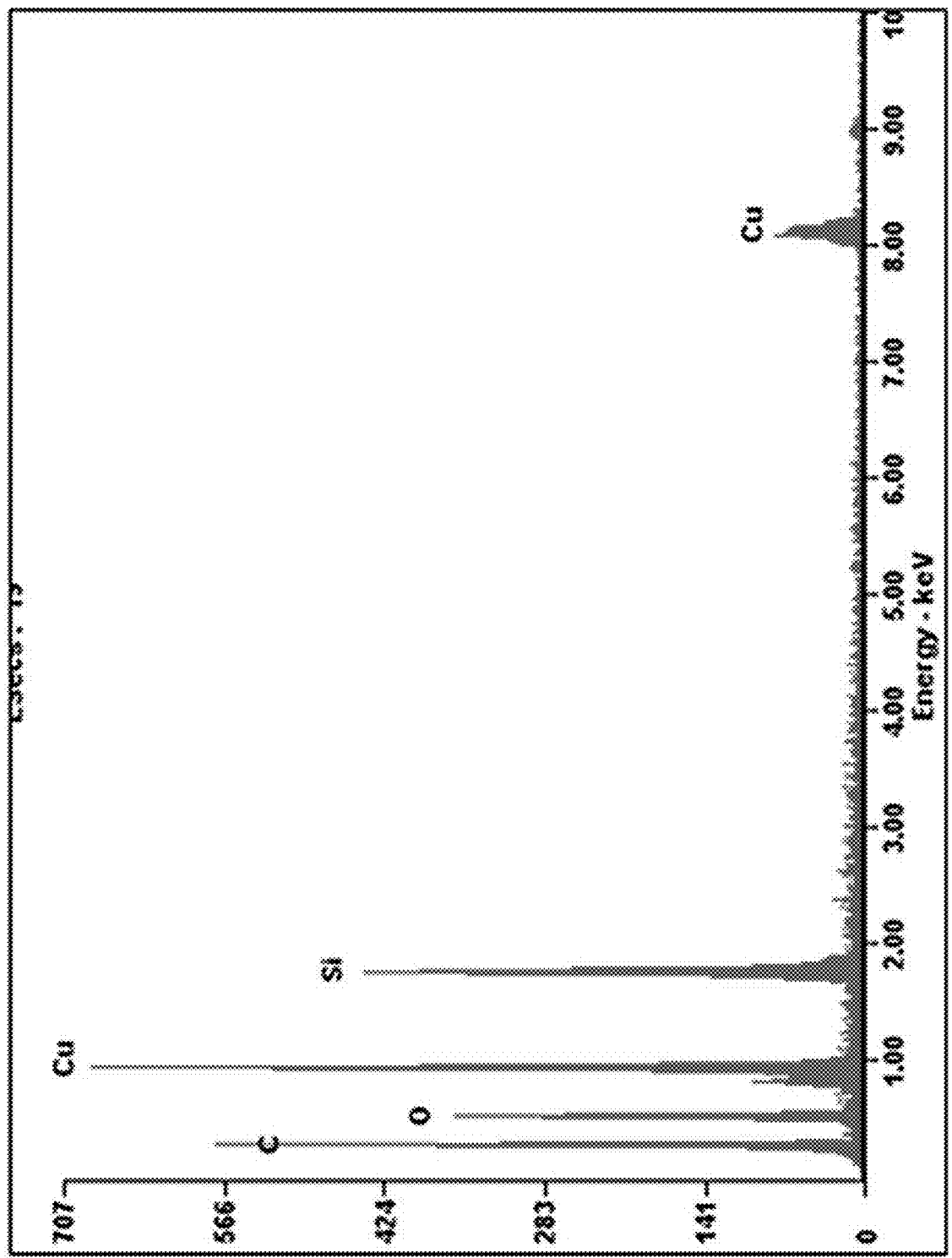

The copper oxide nanoparticles were 20-50 nm in size on SEM images (FIGS. 4A, 4B), and X-ray pattern of copper oxide nanoparticles coated on graphene is shown in FIG. 4C. Additionally, it can be seen that the presence of additional $Cu_2O$ results from oxidation of copper nanoparticles, and Cu metal does not exist and only copper oxide nanoparticles exist. Additionally, it can be seen from EDX results (FIG. 4D) that graphene (C), copper (Cu) and oxygen (O) are included on a silicon (Si) substrate.

Figure 5A:
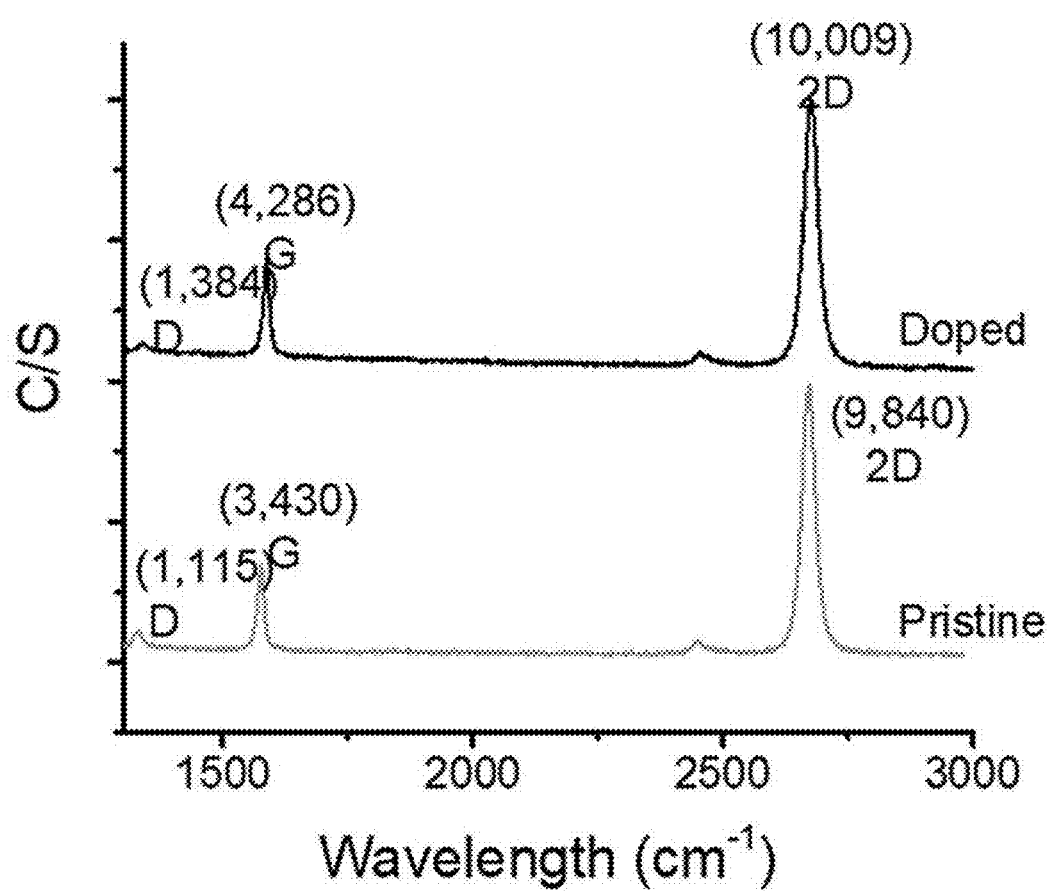
Figure 5B:
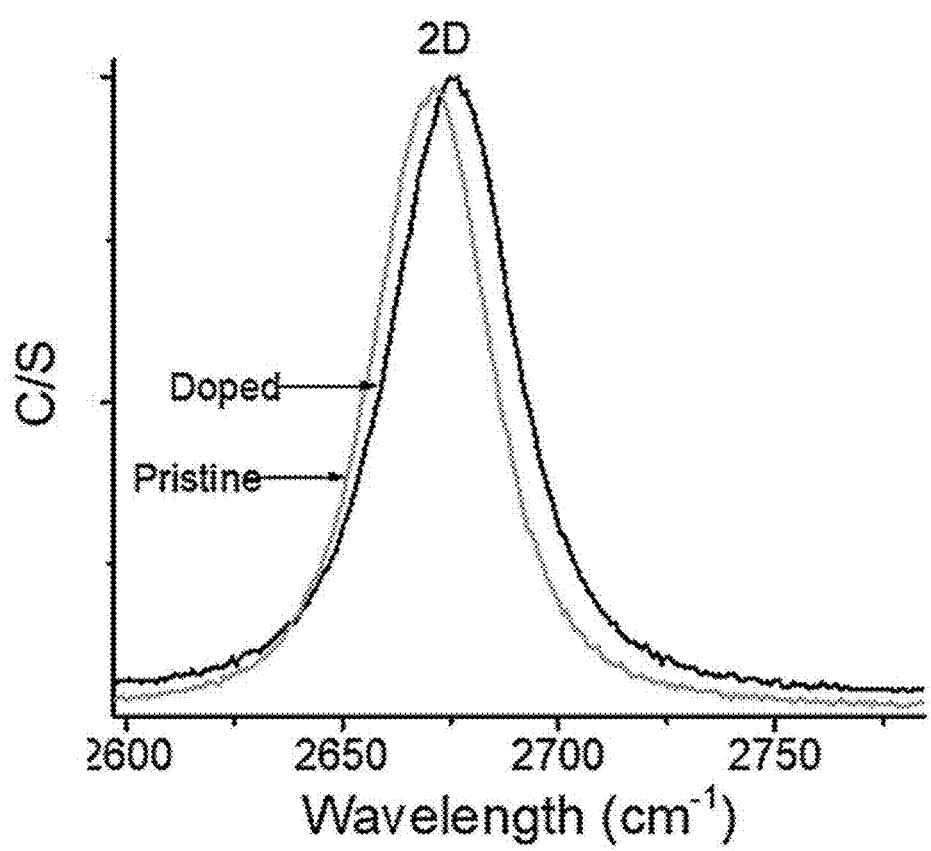

FIG. 5A to FIG. 5C are graphs showing a Raman spectrum of graphene doped with copper oxide according to an embodiment of the present disclosure.

FIG. 5A shows properties comparison and analysis by a comparison of Raman spectra between pristine graphene and graphene doped with copper oxide. The most important properties of graphene appeared in the G band and 2D band. Because both the G band and 2D band are strongly influenced by the concentration of charged particles, both were widely used for doping characterization. In the case of pure graphene, $(I_{2D}/I_G)=2.86$, which corresponds to monolayer graphene.

Additionally, after doping, G peaks and 2D peaks change with changes in the physical and electrical properties of graphene. In this case, $(I_{2D}/I_G)=2.34$. Additionally, as shown in FIGS. 5B and 5C, it can be seen that the chemical environment was changed by copper oxide nanoparticles being doped onto graphene through chemical movements of initial pristine and graphene coated with nanoparticles at 2700 $cm^{-1}$ and 1580 $cm^{-1}$.

Figure 6:
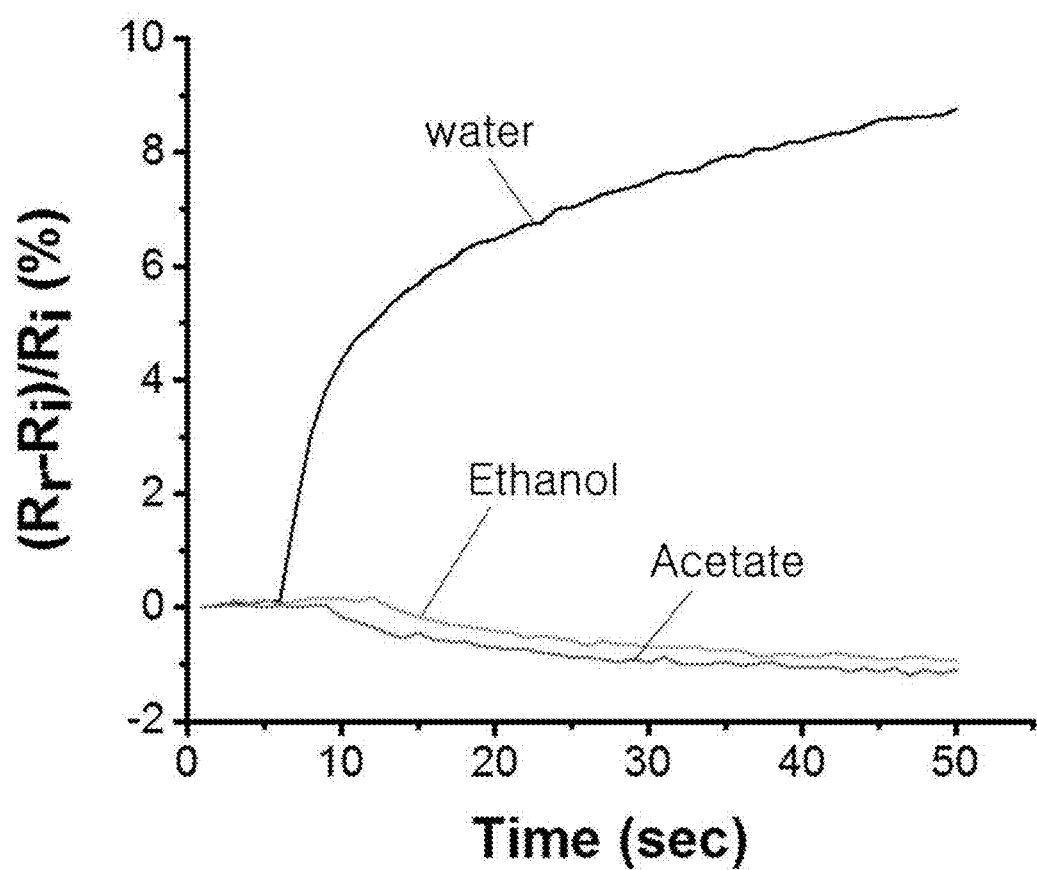
FIG. 6 is a graph showing, in an ammonia gas detection sensor according to an embodiment of the present disclosure, the reactivity of 1 wt % to 2 wt % CuO nanoparticles to an aqueous solution, an ethanol solution and an acetate solution, measured at the ammonia gas concentration of 10 ppm.

FIG. 6 shows the reactivity of 1 wt % to 2 wt % CuO nanoparticles to an aqueous solution, an ethanol solution and an acetate solution, measured at the ammonia gas concentration of 10 ppm.

As shown in FIG. 6, it can be seen that reactivity to each solvent over time continuously increases in water, and rather reduces in the ethanol solution and the acetate solution.

Figure 7:
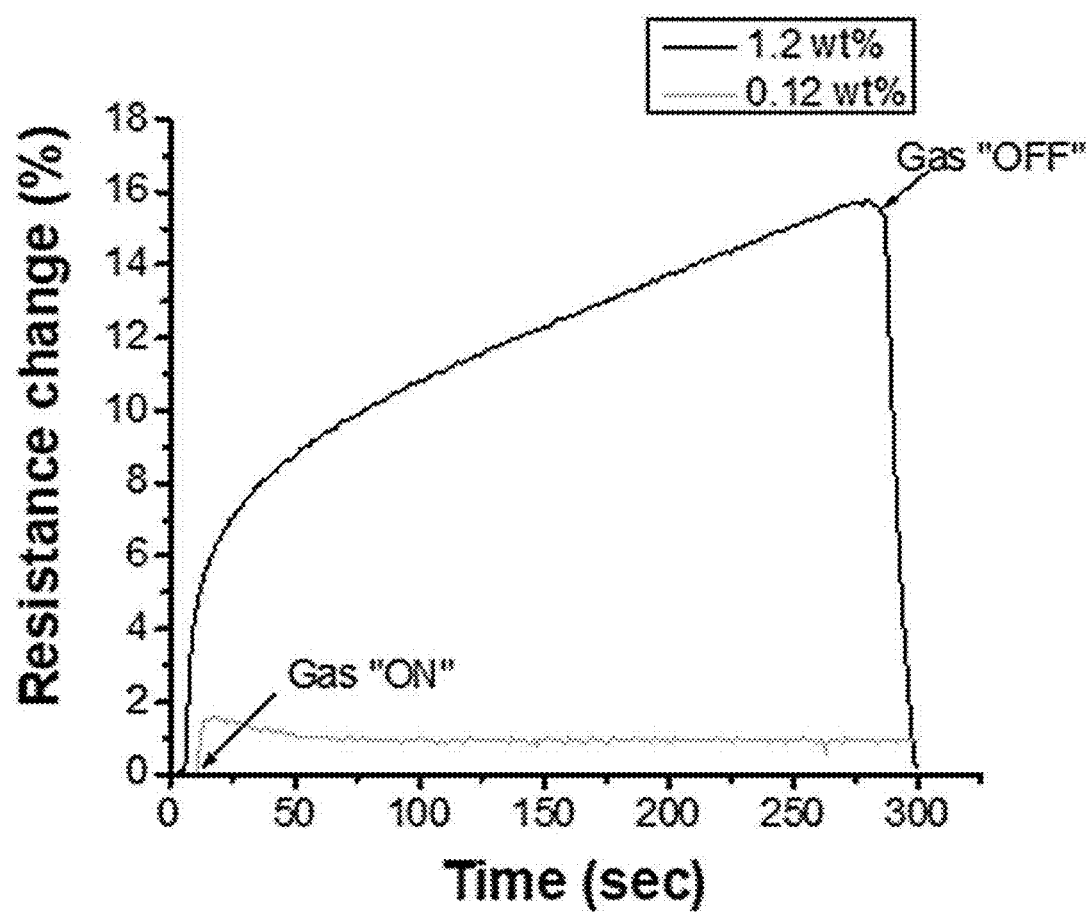
FIG. 7 is a graph showing, in an ammonia gas detection sensor according to an embodiment of the present disclosure, the ammonia gas detection responsivity as a function of the copper oxide nanoparticle concentration.

FIG. 7 is a diagram showing the ammonia gas detection responsivity as a function of the copper oxide nanoparticle concentration according to an embodiment of the present disclosure. FIG. 7 shows the responses of the sensors of pristine graphene and graphene doped with CuO nanoparticles to 100 ppm ammonia gas as a function of time.

Doping of graphene including CuO nanoparticles was performed by selecting 0.12 wt % CuO aqueous solution as a comparative example from 0.05 wt % to 0.15 wt % CuO aqueous solutions, selecting 1.2 wt % CuO aqueous solution as an experimental example from 0.15 wt % to 1.25 wt % CuO aqueous solutions according to an embodiment of the present disclosure, and spin coating 20 μL of each of them on pristine graphene.

As shown in FIG. 7, it can be seen that 1.2 wt % exhibited a big change in reactivity, making it easy to be used to measure ammonia gas, and 0.12 wt % exhibited a change in ammonia gas response within 10 sec from the beginning, but afterwards, resistance values were continuously maintained and were not recovered again, making it impossible to reuse.

Figure 8:
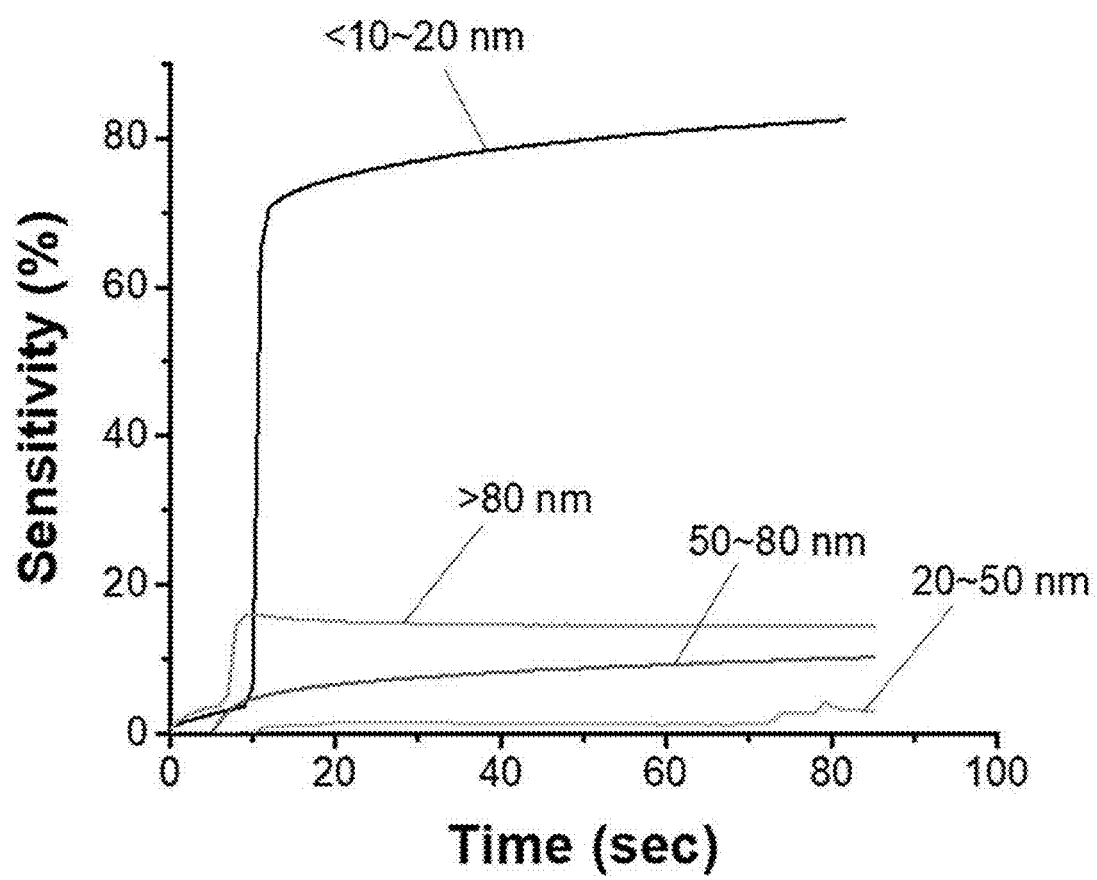
FIG. 8 is a graph showing, in an ammonia gas detection sensor according to an embodiment of the present disclosure, the ammonia gas detection responsivity as a function of the particle size of copper oxide.

FIG. 8 is a graph showing, in the ammonia gas detection sensor according to an embodiment of the present disclosure, the ammonia gas detection responsivity as a function of the particle size of copper oxide.

Measurements were performed at the size of copper oxide nanoparticles of 10 to 20 nm, 20 to 50 nm, 50 to 80 nm, and 80 nm or above, and comparison was performed on the basis of the rotational speed of the spin coater of 1500 rpm.

As shown in FIG. 8, it can be seen that the best sensitivity comes from 10 to 20 nm copper oxide nanoparticles, it was clearly observed that the smaller particles, the higher sensitivity, and it is inferred that the nanoparticle size will increase the chemical reactivity with ammonia gas, extend the reaction contact surface and improve the mechanism of chemical charges.

Figure 9:
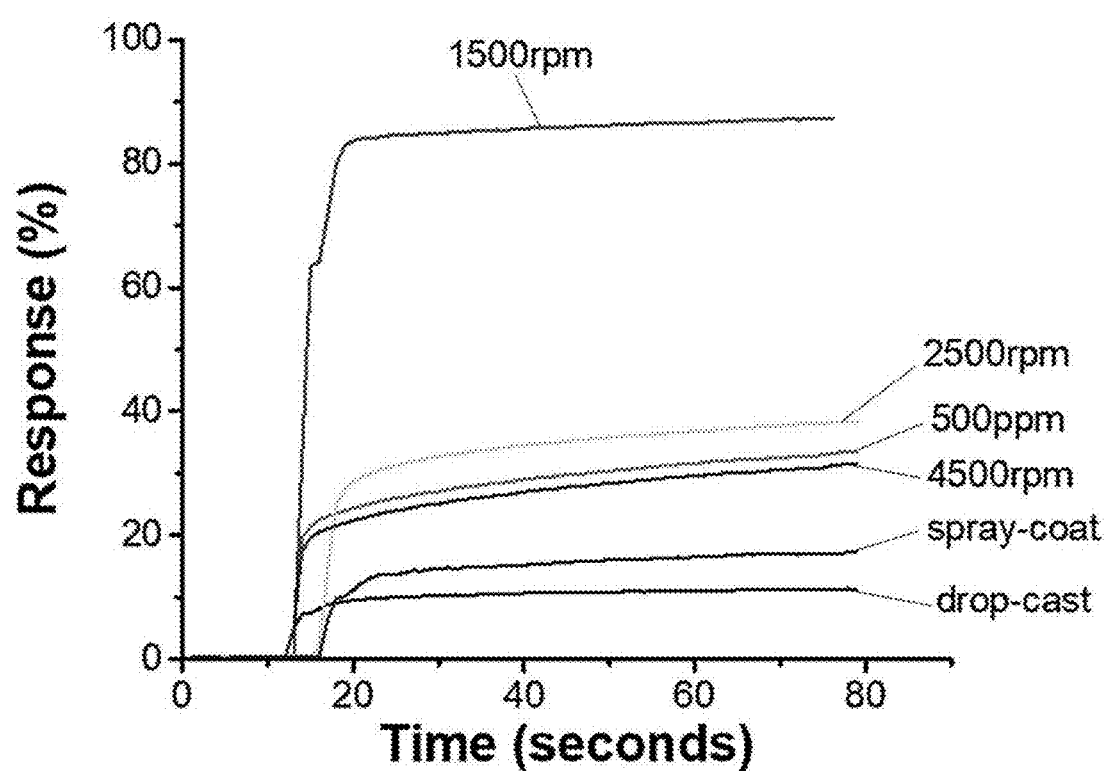
FIG. 9 is a graph showing, in an ammonia gas detection sensor according to an embodiment of the present disclosure, the ammonia gas detection responsivity as a function of the rotational speed (rpm) for spin coating of particles of copper oxide.

FIG. 9 is a graph showing, in the ammonia gas detection sensor according to an embodiment of the present disclosure, the response sensitivity of ammonia gas detection depending on the rotational speed (rpm) of the spin coater for spin coating of particles of copper oxide.

As shown in FIG. 9, the response of the sensor with varying rotational speeds of the spin coater is shown. In this case, a condition for the best sensitivity is that the rotational speed of the spin coater is 1500 rpm. It is determined that various variables such as the surface placement, array and interval of copper oxide nanoparticles doped on graphene are generated according to the spin speed, and this affects the performance of the sensor.

Figure 10A:
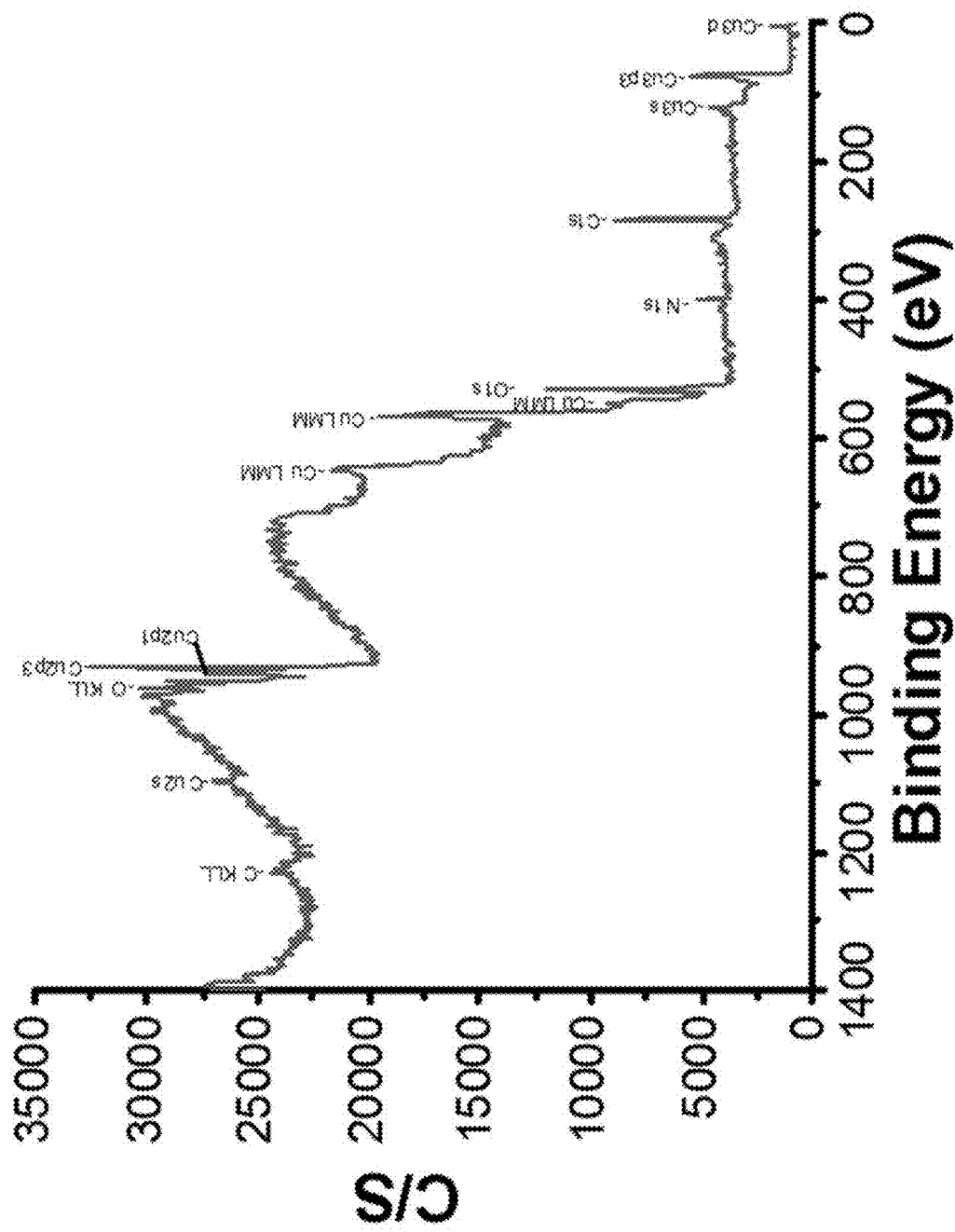

In FIG. 10A to FIG. 10E showing the ammonia gas detection sensor according to an embodiment of the present disclosure, FIG. 10A is an XPS graph showing the observations of the binding reaction structure of pristine graphene and graphene doped with particles of copper oxide with the ammonia gas responsive sensors.

Figure 10D:
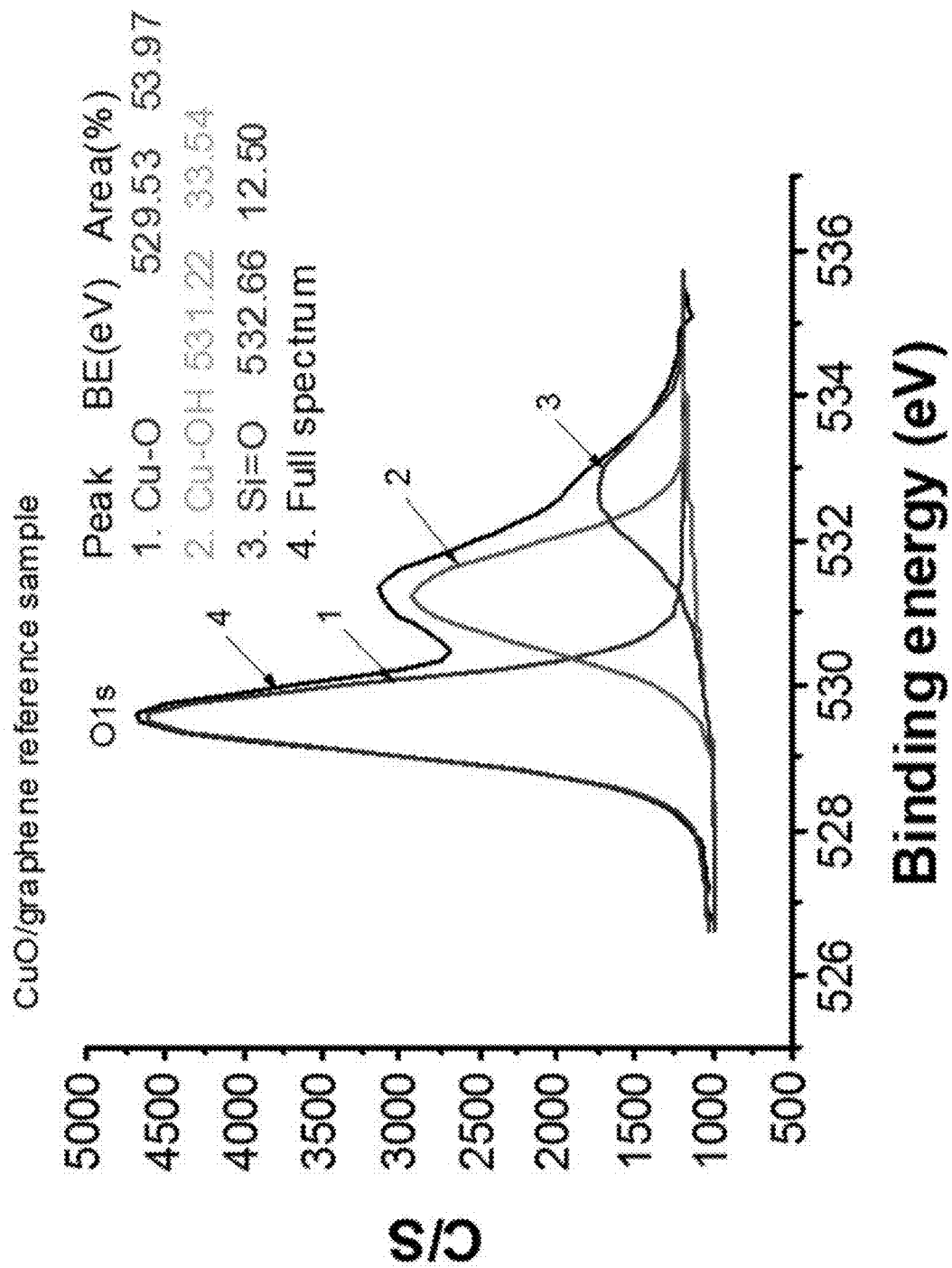
Figure 10E:
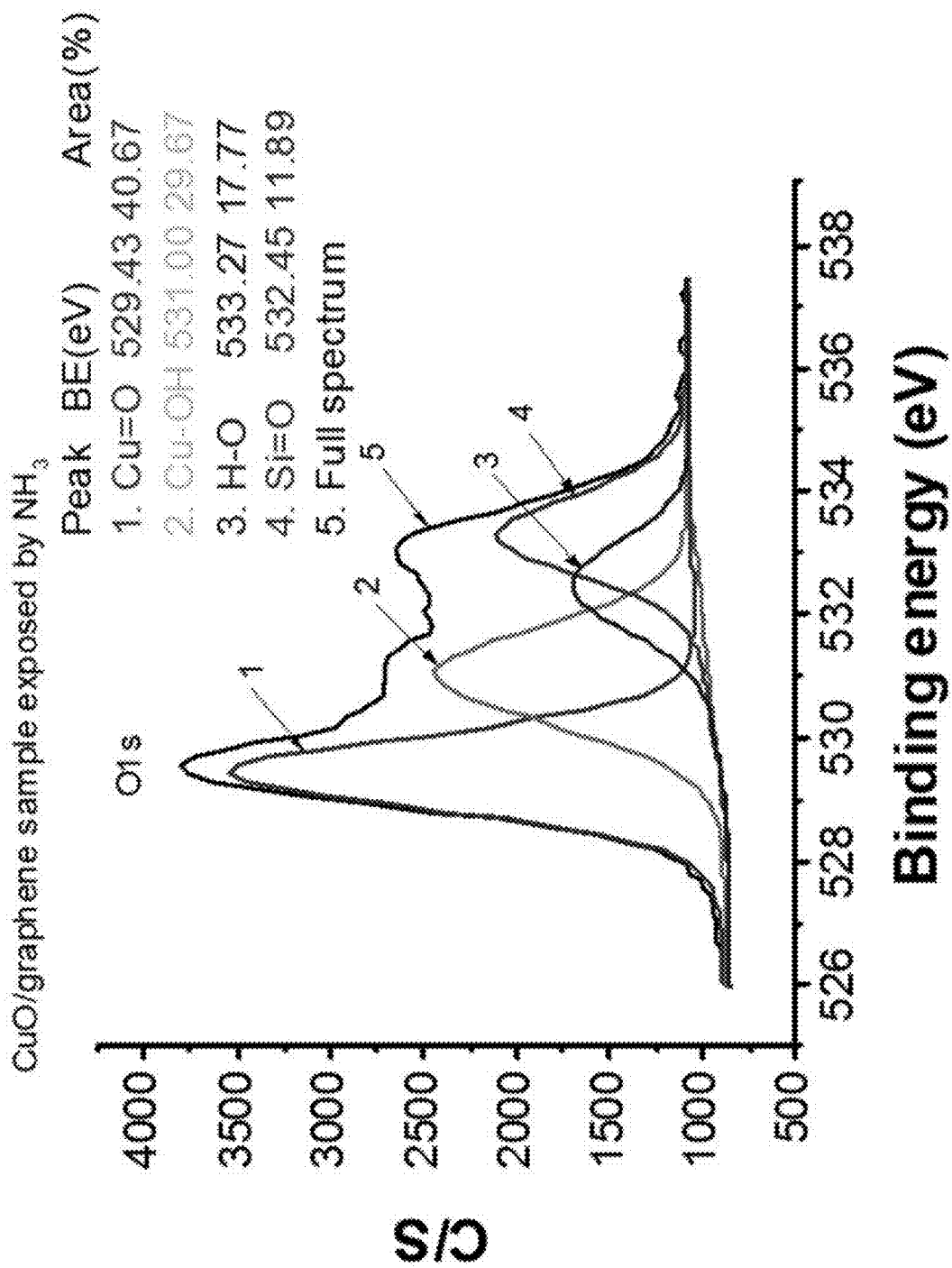

In the XPS spectrum of the CuO-doped graphene sensor, as presented in FIG. 10B, peaks that can be observed up to 284 eV represent that CuO nanoparticles are present on the surface. After the exposure of ammonia gas in the chamber, a sharp peak of C1s did not have a big change. This shows the properties of graphene that do not change even after ammonia is applied (FIGS. 10B, 10C). In FIG. 10D, peaks of 529.53 eV and 531.22 eV come from Cu—O and Cu—OH bonds respectively, and this is because absorbed oxygen of CuO doped onto the graphene surface and —OH groups bind to each other. Due to the Si/Si substrate, a peak of 532.66 eV appeared.

After the exposure of ammonia gas, a new peak of 533.27 eV takes place. This is seen as a water peak appearing due to the reaction mechanism on the sensor surface.

Figure 11:
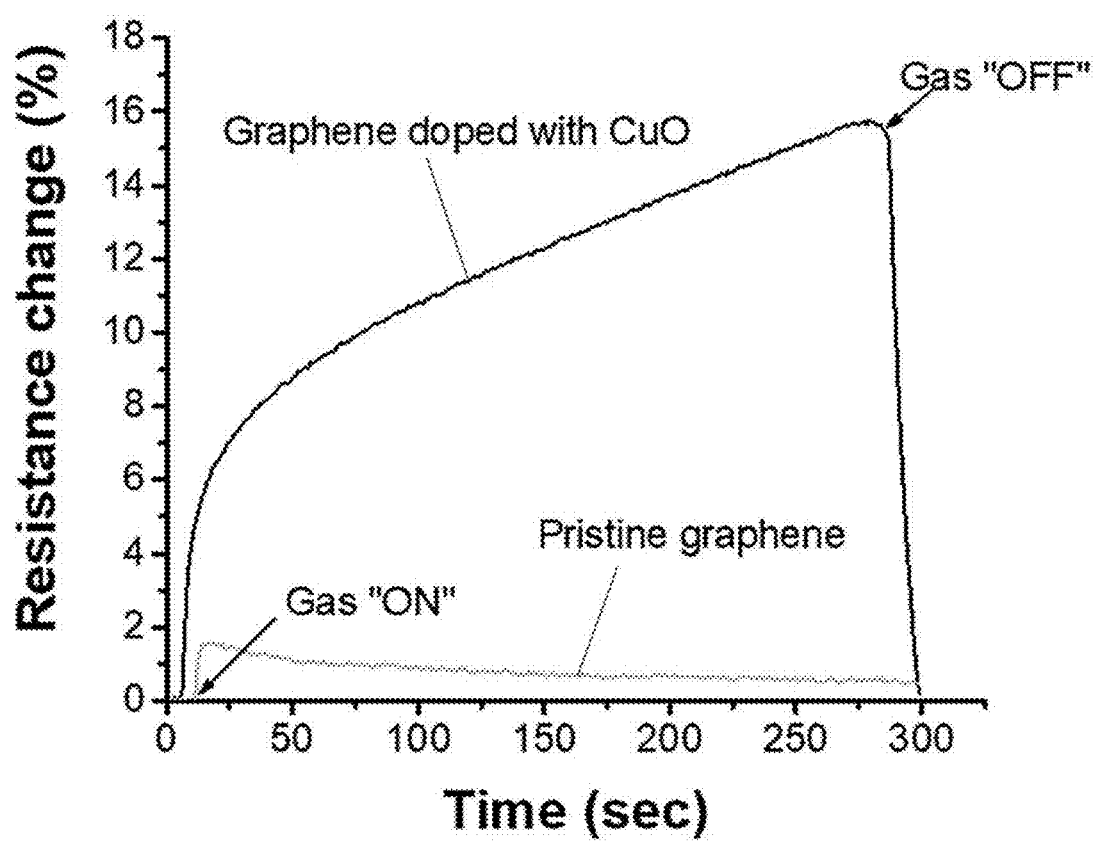
FIG. 11 is a graph showing, in an ammonia gas detection sensor according to an embodiment of the present disclosure, the responses of ammonia gas responsive sensors of pristine graphene and graphene doped with particles of copper oxide.

FIG. 11 is a graph showing, in the ammonia gas detection sensor according to an embodiment of the present disclosure, the response of the sensor when pristine graphene and graphene doped with copper oxide nanoparticles are exposed to ammonia gas.

As a result of measuring the responsivity of the sensors of pristine graphene and graphene doped with copper oxide nanoparticles, as shown in FIG. 11, it can be seen that ammonia responsivity increases 20 times or more within 300 sec. Most of all, one major performance of the sensor, fast recovery after response is needed, and it can be seen that the sensor is recovered to the initial state within 300 sec.

Figure 12:
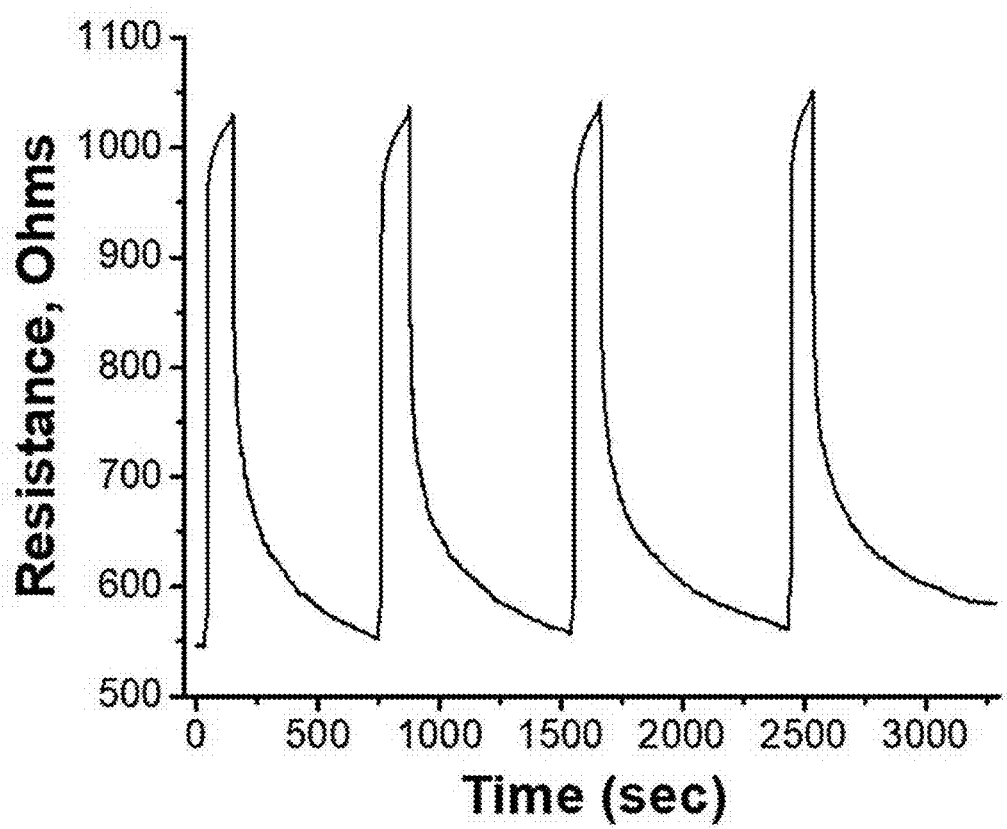
FIG. 12 is a graph showing, in an ammonia gas detection sensor according to an embodiment of the present disclosure, the reproducibility of an ammonia gas responsive sensor.

FIG. 12 is a graph showing, in the ammonia gas detection sensor according to an embodiment of the present disclosure, the reproducibility of sensor response to a predetermined concentration of ammonia gas.

On the basis of the sensor of 10 nm particles coated on graphene, it was allowed to respond to 10 ppm ammonia gas, and the reproducibility of the sensor was measured.

As shown in FIG. 12, when measuring initially and four consecutive times in terms of sensitivity, the responsivity of the sensor was equally measured as 90%, and it can be seen that the reproducibility of the sensor is very good.

Figure 13A:
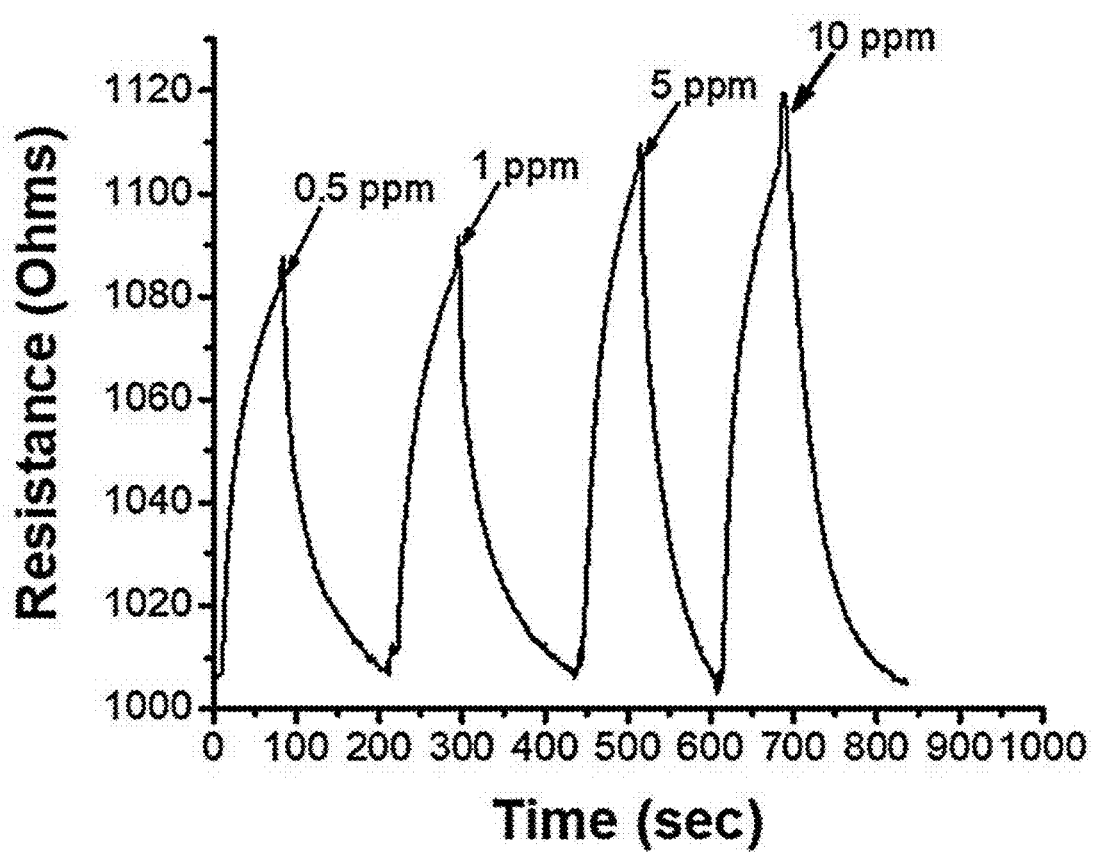
FIG. 13A and FIG. 13B are a graph and a quantitative graph showing responsivity as a function of ammonia gas concentration using an ammonia detection device according to an embodiment of the present disclosure.
Figure 13B:
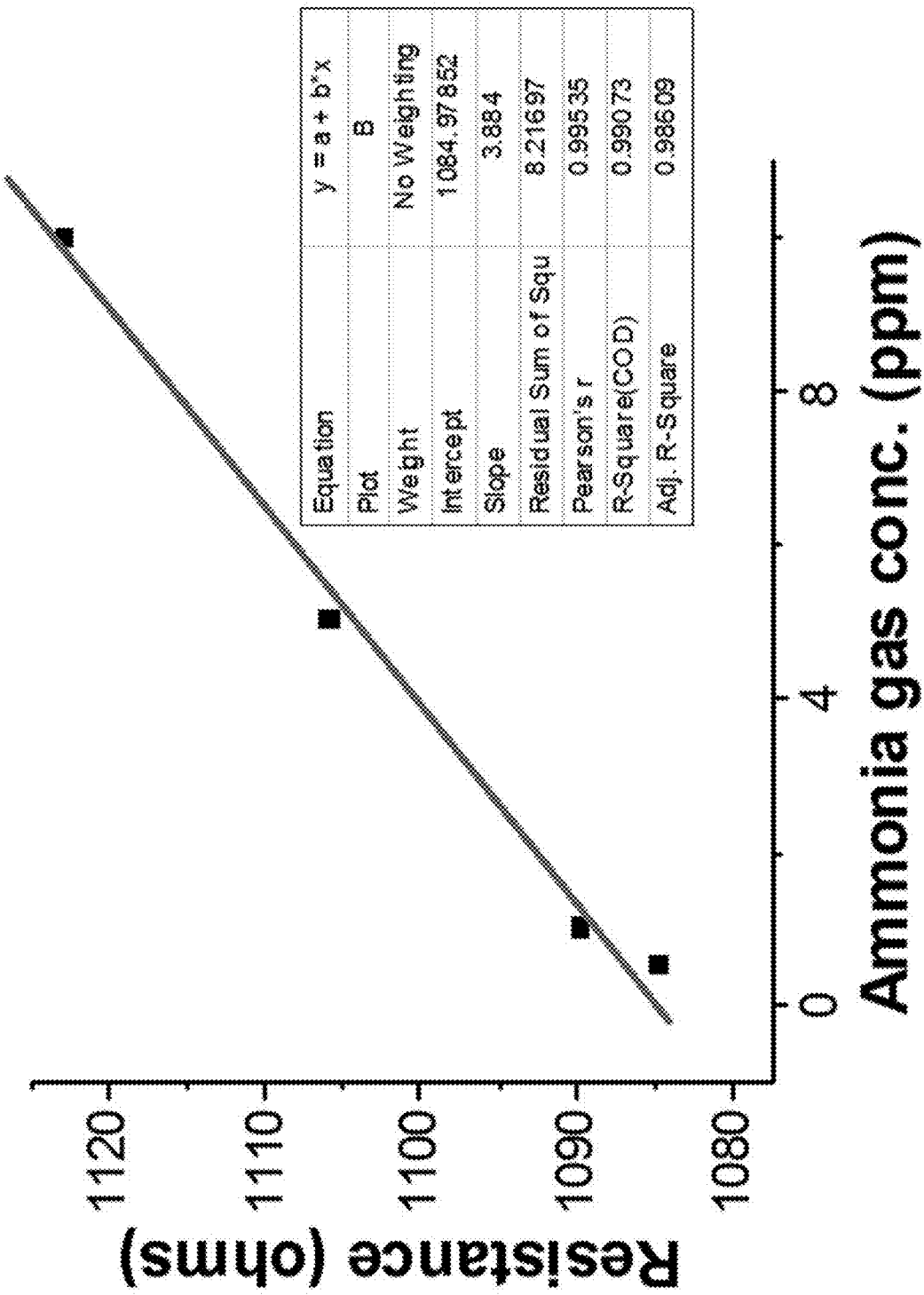

FIG. 13A and FIG. 13B are graphs showing, in the ammonia gas detection sensor according to an embodiment of the present disclosure, quantitativeness of an ammonia gas responsive sensor as a function of concentration.

As shown in FIG. 13A, the response of the sensor as a function of ammonia gas concentration had an increase in measured response resistance value as a function of concentration, and as shown in FIG. 13B, the quantitative curve with concentration changes from 5 ppm to 10 ppm follows Equation of $y=3.884x+1084.978$.

Additionally, the regression curve of 0.990 was very good, and it can be seen that the detection limit is measured as 0.166 (S/N=10) in the present disclosure.

Figure 14:
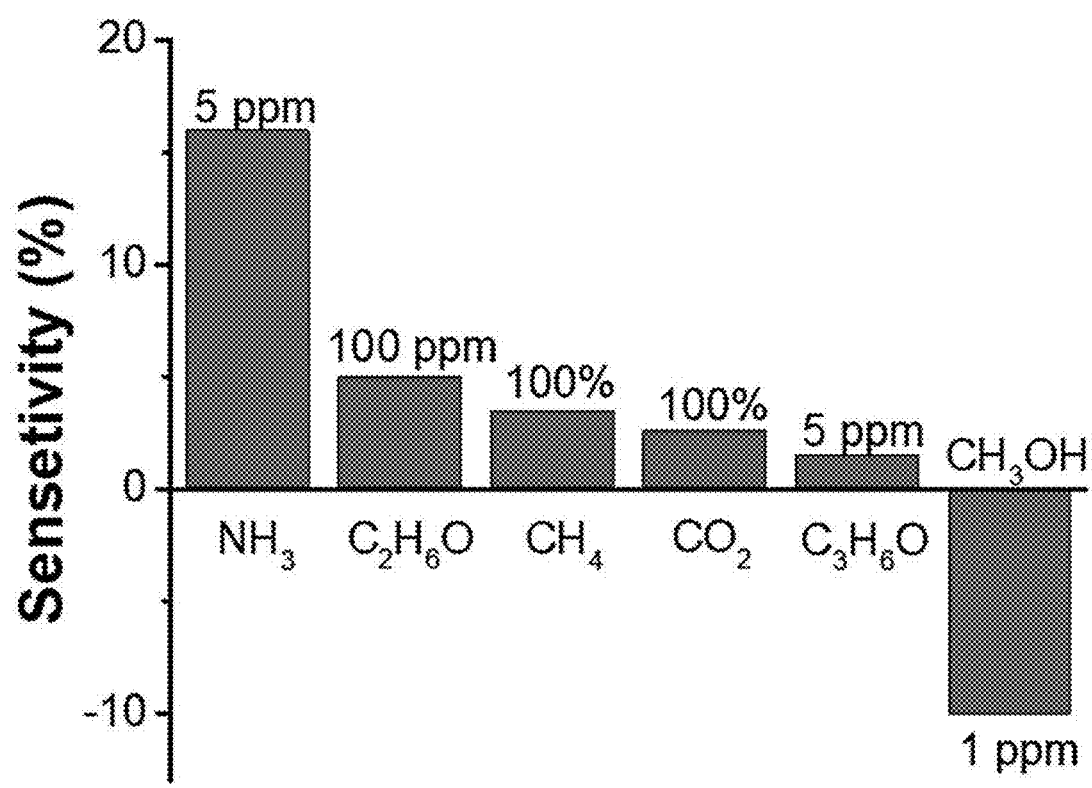
FIG. 14 is a graph showing selectivity through a comparison of responsivity to ammonia gas and other gases using an ammonia gas detection device according to an embodiment of the present disclosure.

FIG. 14 is a graph showing selectivity through a comparison of responsivity to ammonia gas and other gases using an ammonia gas detection device according to an embodiment of the present disclosure.

Various types of gases were used to test the selectivity of the sensor, and the sensor showed selectivity of 5%, 3.5%, 1.5%, −10%, and 2.6% for ethanol, methane, acetone, methanol and carbon dioxide, respectively.

As shown in FIG. 14, it was found that ammonia gas detection has sensitivity that is 40-106 times higher than other gases.

Figure 15:
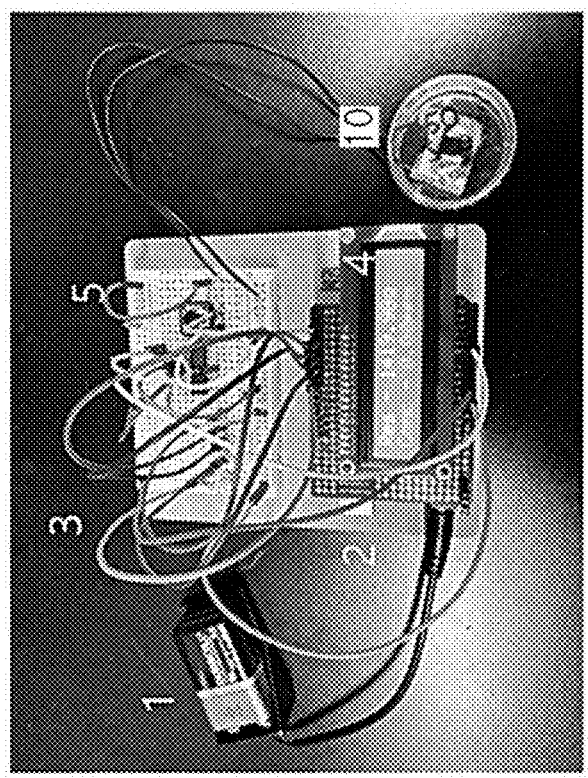
FIG. 15 is a block diagram of a device for ammonia gas detection and a photographic image of a device manufactured based on it.
Figure 15:
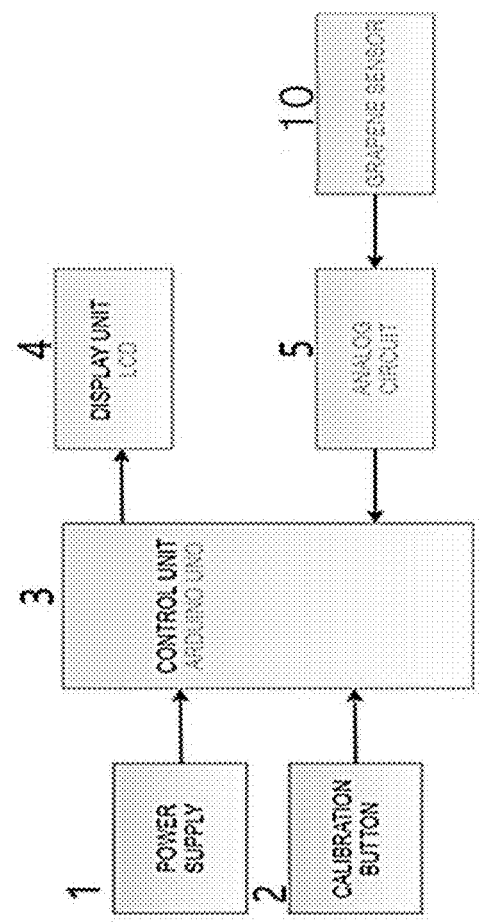
Figure 16:
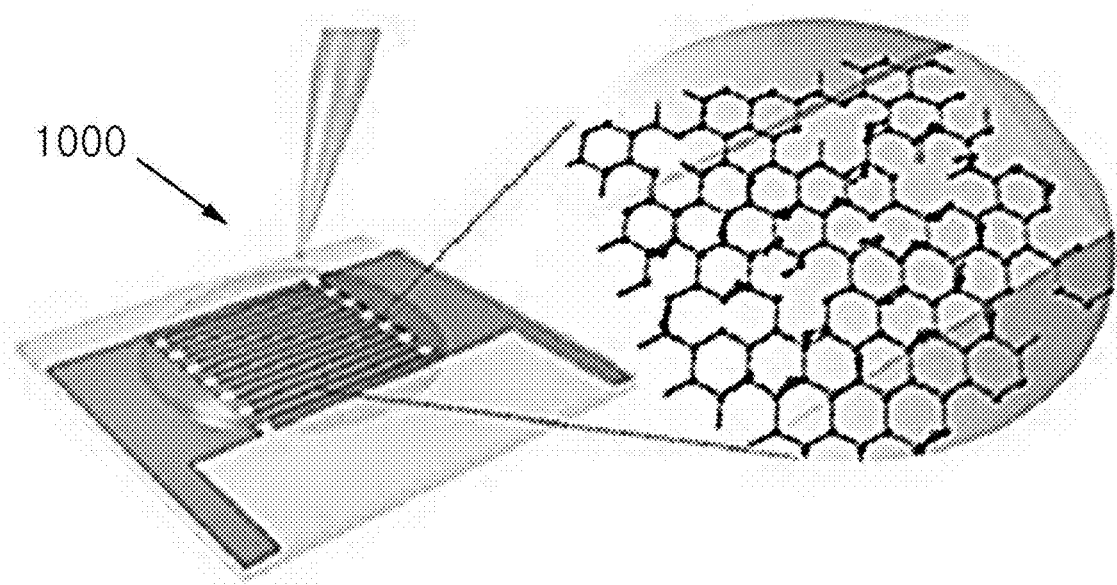
FIG. 16 is a brief illustration of a conventional gas detection sensor.
Figure 17:
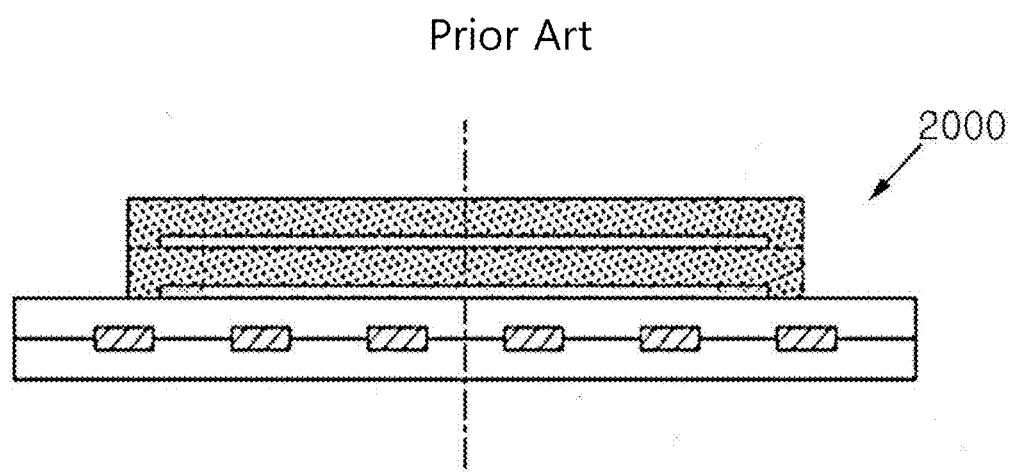
FIG. 17 is a brief illustration of another conventional gas detection sensor.

FIG. 15 is a block diagram of the ammonia gas detection device and a system manufactured based on it. As shown in FIG. 15, it includes a power supply unit 1, a calibration button 2, a control unit 3, a display unit 4, an analog circuit unit 5 and a sensor 10, and a photographic image of a real sensor platform is shown together.

It will be understood by those having ordinary skill in the technical field pertaining to the invention that the present disclosure may be embodied in any other particular forms without departing from the technical idea or the essential feature of the present disclosure with reference to the foregoing description of the present disclosure.

Therefore, it should be understood that the embodiments described herein are for illustration in all aspects, but not intended to limit the present disclosure to the disclosed embodiments, and the scope of the present disclosure is defined by the appended claims rather than the foregoing detailed description, and it should be interpreted that the scope of the present disclosure covers all modifications or variations derived from the spirit and scope of the appended claims and the equivalents to which the appended claims are entitled.

The present disclosure provides a sensor of graphene doped with copper oxide (CuO) with high sensitivity, fast saturation and short recovery time.

What is claimed is:

1. An ammonia gas detection sensor, comprising:
a substrate;
a graphene sheet disposed on the substrate; and
metal nanoparticles disposed on the graphene sheet;
wherein the graphene sheet is a monolayer; and
wherein the metal nanoparticles include copper oxide (I) (CuO) nanoparticles having a size of 10 nm to 20 nm;
wherein the CuO nanoparticles are formed by doping a mixed solution including CuO nanoparticles onto the graphene sheet; and
wherein the mixed solution includes 1 wt % to 2 wt % of the CuO nanoparticles based on the total weight.

2. The ammonia gas detection sensor according to claim 1, wherein the ammonia gas is a gaseous ammonia gas.

3. The ammonia gas detection sensor according to claim 1, wherein the graphene sheet is deposited on the substrate by a chemical vapor deposition method.

4. The ammonia gas detection sensor according to claim 1, wherein the doping includes dipping the graphene sheet in the mixed solution and stirring the mixed solution by rotation at 1000 rpm to 2000 rpm.

5. An ammonia gas detection device, comprising:
the ammonia gas detection sensor according to claim 1;
electrodes connected to two ends of the graphene sheet; and
a power supply unit which operates the ammonia gas detection sensor.

6. The ammonia gas detection sensor according to claim 1, wherein the mixed solution is aqueous.

* * * * *